(12) United States Patent
Bovetto et al.

(10) Patent No.: US 8,012,509 B2
(45) Date of Patent: Sep. 6, 2011

(54) MILK FRACTIONS AND MILK PREPARATIONS FOR TREATING AND/OR PREVENTING COX-2 MEDIATED DISEASES

(75) Inventors: Lionel Bovetto, Larringes (FR); Joerg Hau, Cuarnens (CH); Catherine Mace, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/571,959

(22) PCT Filed: Sep. 13, 2004

(86) PCT No.: PCT/EP2004/010200
§ 371 (c)(1),
(2), (4) Date: Dec. 4, 2006

(87) PCT Pub. No.: WO2005/025335
PCT Pub. Date: Mar. 24, 2005

(65) Prior Publication Data
US 2007/0110818 A1 May 17, 2007

(30) Foreign Application Priority Data
Sep. 12, 2003 (EP) .................................. 03020739

(51) Int. Cl.
*A61K 35/20* (2006.01)
(52) U.S. Cl. ........... 424/535; 514/5.5; 514/5.6; 514/5.7; 514/16.6; 514/19.4
(58) Field of Classification Search .................. None
See application file for complete search history.

(56) References Cited

U.S. PATENT DOCUMENTS

| | | | | |
|---|---|---|---|---|
| 4,358,464 | A * | 11/1982 | Soehnlen | 426/41 |
| 5,061,622 | A * | 10/1991 | Dosako et al. | 435/68.1 |
| 5,147,853 | A * | 9/1992 | Dosako et al. | 514/7 |
| 6,465,509 | B2 * | 10/2002 | Li et al. | 514/460 |
| 6,469,063 | B1 | 10/2002 | Bleich et al. | |
| 6,589,574 | B2 * | 7/2003 | Swamylingappa et al. | 426/34 |
| 2002/0169195 | A1 * | 11/2002 | Kindness et al. | 514/406 |
| 2003/0026845 | A1 * | 2/2003 | Etzel et al. | 424/535 |

FOREIGN PATENT DOCUMENTS

| | | |
|---|---|---|
| WO | WO 01/11990 | 2/2001 |
| WO | WO 01/56555 | 8/2001 |
| WO | WO 02/051437 | 7/2002 |

OTHER PUBLICATIONS

Colker et al., Nutrition, May 2002, vol. 18, p. 388-392.*
Imam et al., Biochem. J., 1981, vol. 193, 47-54.*
Najera et al., Food Chemistry, 2003, vol. 80, No. 3, p. 345-352.*
Huffman et al., Journal of Dairy Science, 1999, vol. 82, No. 10 p. 2238-2244.*
Kester et al., Dairy Sci, 1984, vol. 67, p. 2757-2774.*
Tsuda et al., Mutation Research, 2000, vol. 462, p. 227-233.*
Kim et al., J Environ. Pathol. Toxicol. Oncol., 2002, vol. 21, No. 2, Abstract.*
Imam et al. (Biochem. J., 1981, vol. 193, 47-54.*
Butterfield et al., Journal of Nutritional Biochemistry, 2002, vol. 13, p. 444-461.*
Huffman et al., Journal of Dairy Science, 1999, vol. 82, No. 10 p. 2238-2244.*
Abd El-Salam et al., Int. Dairy Journal, 1996, vol. 6, p. 327-341.*
Brody E.P., British Journal of Nutrition, 2000, vol. 84, Suppl.1, p. S39-S46.*
Chen et al., Am J Physiol Lung Cell Mol Physiol, 2001, vol. 280, p. L450-L457.*
Huffman et al., J Dairy Sci, 1999, vol. 82 p. 2238-2244.*
Scaloni et al., Biochimica et Biophysica Acta, 2002, vol. 1598, p. 30-39.*
Tsuda et al., Mutation Research, 2000, vol. 462, p. 227-233.*

* cited by examiner

*Primary Examiner* — Kade Ariani
(74) *Attorney, Agent, or Firm* — K&L Gates LLP (57) ABSTRACT

The present invention pertains to nutritional and pharmaceutical compositions for treating and preventing cyclooxygenase-2 mediated diseases and to a process for increasing the cyclooxygenase-2 inhibiting activity of a product. In addition thereto, the present invention relates to the use of one ore more milk protein fractions and/or one ore more milk protein preparations for inhibiting the activity of cyclooxygenase-2 (COX-2), in particular for the preparation of a medicament or a functional food for treating and preventing cyclooxygenase-2 mediated diseases.

10 Claims, 4 Drawing Sheets

MILK FRACTIONS AND MILK PREPARATIONS FOR TREATING AND/OR PREVENTING COX-2 MEDIATED DISEASES

BACKGROUND

The present invention pertains to nutritional and pharmaceutical compositions for treating and/or preventing cyclooxygenase-2 mediated diseases and to a process for increasing the cyclooxygenase-2 inhibiting activity of a product. In particular, the present invention also relates to the use of one ore more milk protein fractions and/or one ore more milk protein preparations for inhibiting the activity of cyclooxygenase-2, specifically for the preparation of a food product or a medicament for treating and/or preventing cyclooxygenase-2 mediated diseases.

Cyclooxygenase (COX) enzymes are key enzymes required for the conversion of arachidonic acid to prostaglandins (PGs). Two isoforms of COX have been identified so far, COX-1 and COX-2, which differ in many respects: COX-1 is expressed constitutively in most tissues and is presumed to be responsible for the production of prostaglandins that control normal physiological functions, such as the maintenance of the gastric mucosa and the regulation of renal blood flow. The second isoform, COX-2, does not seem to be constitutively expressed in most of the normal tissues, but is highly inducible and may be found at particular locations only, e.g. at sites of inflammation and in cancer cells.

Although COX-enzymes are found to be membrane-bound, they do not have a conventional trans-membrane region. Instead, they contain four amphipathic helices juxtaposed to form a region of hydrophobicity. This hydrophobic region anchors the "lower" portion of the enzyme in the membrane. The active site of cyclooxygenase is located in the area of hydrophobicity near the amphipathic helices. Substrate and inhibitors of the enzyme are considered to reach the active site via a channel embodied in the lipid bilayer (W. Krause, R. N. Dubois, *Prostaglandins & other Lipid Mediators* 61 (2000), 145-161).

COX-inhibitors, and in particular COX-2 inhibitors, are used to treat a variety of different diseases, such as inflammatory diseases, and are also used as analgesics. In addition, it has been found that COX-2 is commonly over-expressed in premalignant and malignant tissues and a treatment with COX-2 inhibitors has been shown to reduce the formation of intestinal, esophageal, tongue, breast, skin, lung and bladder tumors in animals (K. Subbaramaiah, A. J. Dannenberg, *TRENDS in Pharmacological Sciences* 24 (2003), 96-102).

Various well known non-steroidal anti-inflammatory drugs (so called NSAIDs), such as e.g. aspirin and ibuprofen, inhibit COX-1 and COX-2. Recently, a new class of inhibitors (COXIBs) has been described which specifically inhibits the COX-2 enzyme only (M. E. Turini, R. N. Dubois, *Physiology And Diseases. Annu. Rev. Med.* 53 (2002), 35-57). However, NSAIDs are known to cause serious side-effects, e.g. renal problems and duodenal and stomach ulceration.

SUMMARY

Consequently, the problem of the present invention is to provide additional means for inhibiting cyclooxygenases, in particular COX-2, which means should be associated with a low risk of deleterious side effects.

This problem has been solved by providing specific fractions and/or preparation of milk which exhibit a COX-2 inhibiting activity, for the treatment and/or prevention of diseases mediated by COX-2.

Additional features and advantages are described herein, and will be apparent from, the following Detailed Description and the figures

DETAILED DESCRIPTION

Figure 1:
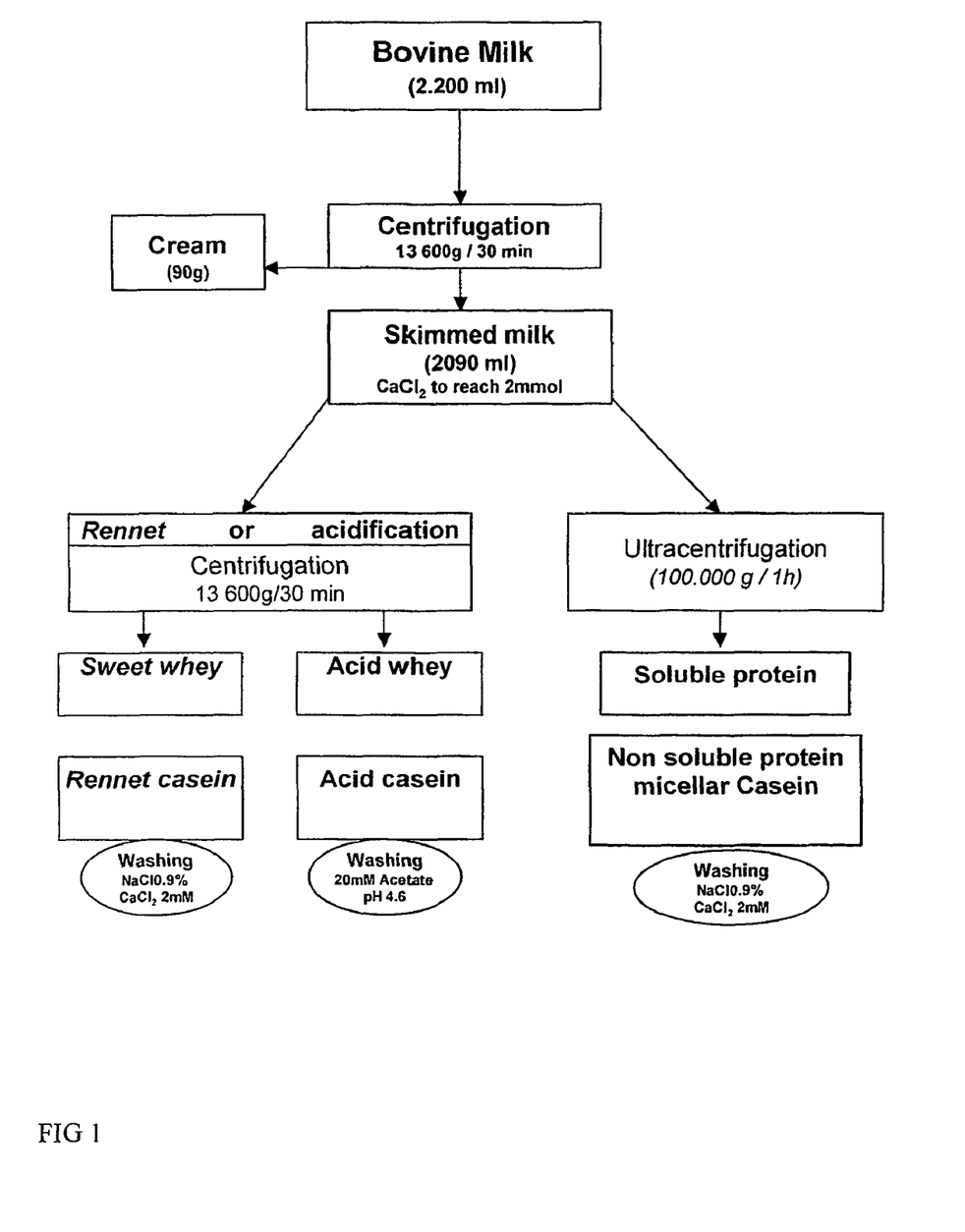
FIG. 1 is a diagram showing the preparation of bovine milk fractions as outlined in Example 1.1.
Figure 2:
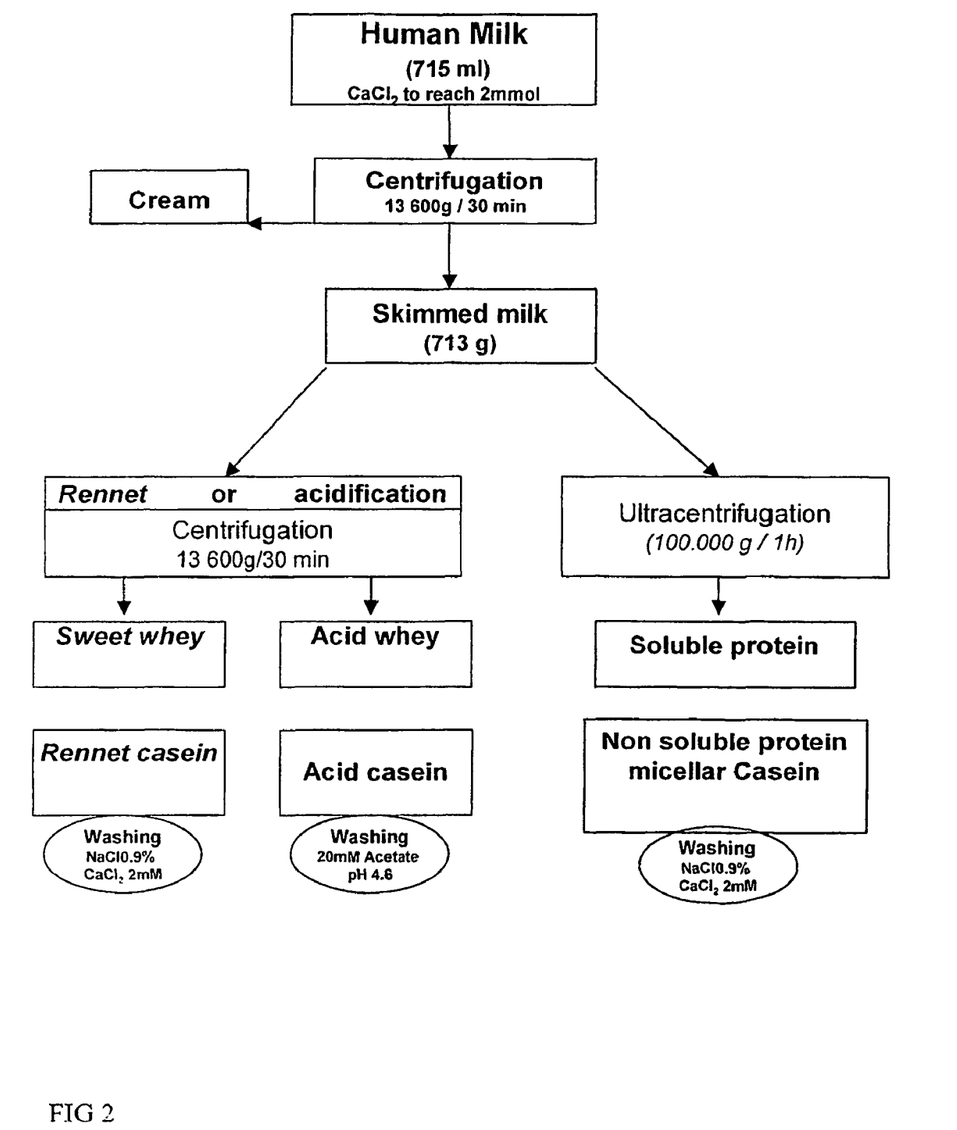
FIG. 2 is a diagram showing the preparation of human milk fractions as outlined in Example 1.2.
Figure 3:
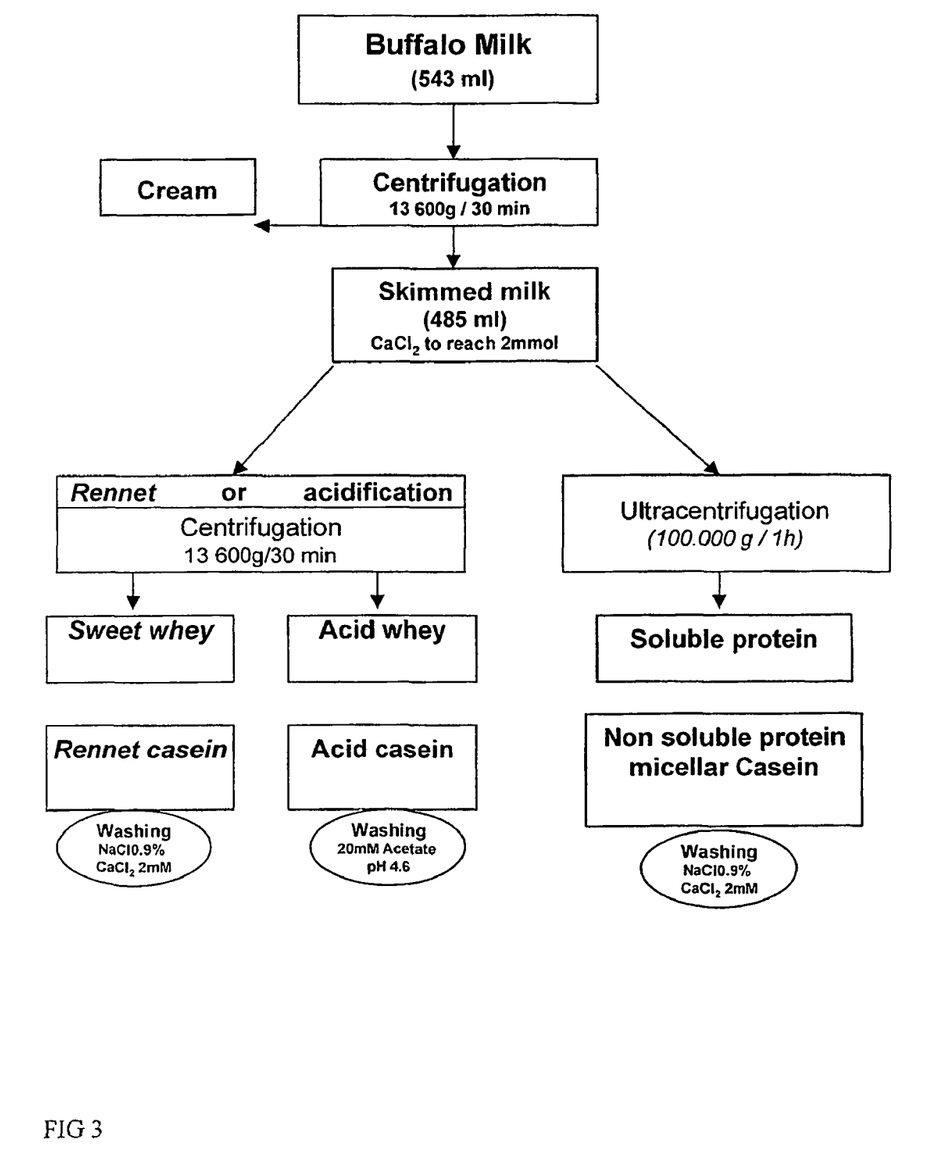
FIG. 3 is a diagram showing the preparation of buffalo milk fractions as outlined in Example 1.3.
Figure 4:
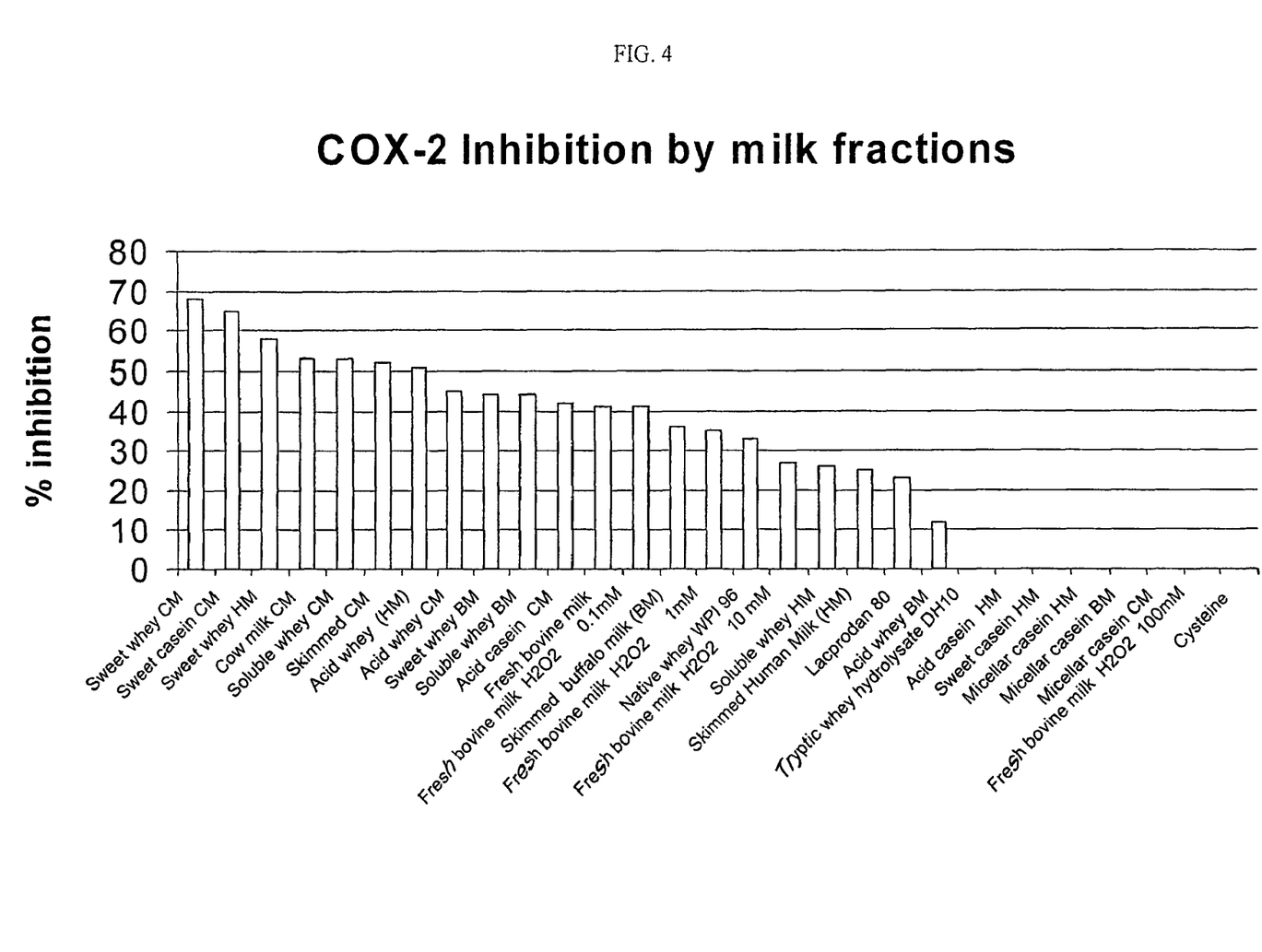
FIG. 4 shows a comparison of the COX-2 inhibiting activities of various milk protein fractions and milk protein preparations derived from human milk (HM), cow's milk (CM) and buffalo milk (BM).

According to one aspect, the present invention provides a nutritional and/or a pharmaceutical composition for treating and/or preventing cyclooxygenase-2 mediated diseases, said composition comprising a therapeutically effective amount of one or more milk protein fractions and/or one or more milk protein preparations, which provide a cyclooxygenase-2 inhibiting activity.

The term "treating and/or preventing cyclooxygenase-2 mediated diseases" as used in the present application comprises both, treating a disease associated with the expression, in particular with an increased expression of cyclooxygenase-2, as well as preventing a disease which may be influenced by reducing the level of cyclooxygenase-2 at a specific site in the body of an individual, or by preventing a rise of the level of cyclooxygenase-2 at a specific site in the body of an individual. An increased level of cyclooxygenase-2 designates an amount, which is superior to the level of cyclooxygenase-2 statistically present in a healthy individual at a specific site in average.

A first group of cyclooxygenase-2 mediated diseases, which may be treated and/or the onset thereof may be prevented according to the present invention is cancer, comprising any of its pre-cancerous states. According to the scientific data at hand it is presently assumed that in pre-malignant and malignant tissues COX-2 is over-expressed, and that such increased expression of COX-2 being associated at least in part in the induction of tumor formation. In fact, such an over-expression of COX-2 has been observed in several pre-malignant and malignant conditions in organs such as e.g. colon, stomach, esophagus, liver, biliary stem, pancreas, head and neck, lung, breast, bladder, female genital organs' and skin. Also, a successful treatment of tumors on the basis of COX-2 inhibitors of the prior art has been achieved already. Thus, administration of a composition according to the present invention will be helpful in treating and/or preventing cancer and/or pre-cancerous states.

Also, COX-2 inhibitors have been shown to block formation of prostaglandins, the presence of which is associated with the development and progress of pain, fever and inflammation. Additional target groups of cyclooxygenase-2 mediated diseases, for which according to the present invention a treatment and/or prevention is aimed at, are arthritis, rheumatic fever, symptoms associated with influenza or other viral infections, dysmenorrhoea, headache, toothache, degenerative joint diseases, etc. Also Alzheimer's disease is considered to be a target disease according to the present invention, since COX-2 inhibitors have been shown to have a protective effect on the development of this disease.

The nutritional and/or pharmaceutical compositions according to the present invention are designed to be administered to any individual in need thereof, preferably mammals, in particular humans and animals, e.g. pets.

A "cyclooxygenase-2 inhibiting activity" as mentioned herein may be determined according to a COX-2 screening method on the basis of HUV-EC-C cells as indicated in the examples, below, but also on the basis of other assays known in the art.

The therapeutically effective amount of one or more milk protein fractions and/or one or more milk protein preparations specifically required for a given individual may easily be determined by the skilled artisan according to his general knowledge in the art considering a variety of factors, such as body weight, age, general health, sex, diet, time of administration, route of administration, rate of excretion, drug combination, etc. Basically, the special dosage regimen for a particular individual will depend on the fact, whether a general prevention or an acute treatment of a disease is aimed at. For example, the daily dosage of said one or more milk protein fractions and/or one or more milk protein preparations may be chosen from between 7 mg to 70 g in case of a person of 70 kg, corresponding to a daily dosage of from about 0.1 mg to about 1 g per kilo of body weight, preferably from about 0.5 mg to about 100 mg, more preferably from about 5 mg to about to 70 mg and even more preferably from about 10 mg to about 50 mg.

A nutritional composition according to the present invention is any composition suitable for human or animal consumption, comprising at least one material selected form the group consisting of water, proteins and/or peptides, carbohydrates, fats.

A pharmaceutical composition according to the present invention is any composition comprising at least one therapeutically active compound as detailed herein.

Moreover, the present invention provides a nutritional and/or pharmaceutical composition which comprises an increased amount of said one or more milk protein fractions and/or one or more milk protein preparations providing a cyclooxygenase-2 inhibiting activity, and which provides a cyclooxygenase-2 inhibiting activity which is higher than the cyclooxygenase-2 inhibiting activity of a nutritional and/or pharmaceutical composition wherein the amount of said one or more milk protein fractions and/or one or more milk protein preparations has not been increased.

Such an increased amount of said one or more milk protein fractions and/or one or more milk protein preparations providing a cyclooxygenase-2 inhibiting activity may be obtained either by adding an additional amount of said one or more milk protein fractions and/or one or more milk protein preparations and/or by substituting a milk fraction with a milk fraction wherein the bio-active compound(s) have been enriched. An enrichment may be achieved according to physical, chemical and biological techniques well known in the art and may be carried out e.g. on the basis of the assay described in the examples.

The cyclooxygenase-2 inhibiting activity of a product resulting from an enrichment or addition as outlined above should be for example at least 1%, more preferably at least 5%, most preferably at least 10% higher, and in particular at least 25% higher as the cyclooxygenase-2 inhibiting activity of the reference nutritional/pharmaceutical composition, i.e. of the nutritional/pharmaceutical composition having—apart of the additional and/or enriched one or more milk protein fractions and/or one or more milk protein preparations—the same composition as the nutritional/pharmaceutical composition having an increased cyclooxygenase-2 inhibiting activity.

During extensive studies, the present inventors demonstrated that specific milk protein fractions, provide a cyclooxygenase-2 inhibiting activity, which essentially may not be found in or exceeds that of milk as such. Without wishing to be bound to any theory, it may be supposed that the low initial activity observed in human milk seems to be associated with serum proteins. The caseins themselves might have a suppressive effect, or contain a "latent bioactivity" which is activated (and then found in the whey fraction) by acidification or rennet treatment.

As the said milk fractions found to exhibit an increased COX-2 inhibiting activity whey fractions of human milk, bovine milk, buffalo milk, or of another mammalian milk, skimmed milk fraction of human milk, bovine milk, buffalo milk, bovine milk, or of another mammalian milk, acid casein fraction of bovine milk, sweet casein fraction of bovine milk, etc. or combinations thereof may be mentioned. As whey fractions, e.g. acid whey fractions, sweet whey fractions, soluble whey fractions and combinations thereof may be used.

Additional sub-fractionation of soluble whey protein and screening reveals that some sub-fractions of soluble whey protein from bovine milk are preferred.

In principle, separation and isolation of sub-fractions of soluble whey protein may be achieved by hydrophobic interaction chromatography (HIC), or by hydrophobic interaction high performance liquid chromatography (HI-HPLC), reversed-phase high-performance liquid chromatography (RP-HPLC), and the like, all of which are based on the same separation principles, for example. The principles of HIC are known to the skilled person. Generally, samples are loaded onto an equilibrated column (stationery phase) comprising a hydrophobic material retaining the samples. The hydrophobic material may be, for example, macroporous crosslinked polystyrene, commercialized as Amberlite Xad 16 XAD 16 from Rohm and Hass, for example. 15 RPC TN 17-0727-02 (polystyrene-divinylbenzene) from Amersham or equivalents may also be used.

Before the protein is loaded onto the column, the latter may be equilibrated with a buffer. After the fraction is loaded, a buffer or a mixture of buffers (mobile phase) may be run over the column, whereby the mixture of buffers varies and may have, therefore, varying properties of eluting protein sub-fractions according to their hydrophobicity from the column. Separation of whey proteins according to this method is described in: "Simultaneous separation and quantitation of the major bovine whey proteins including proteose peptone and caseinomacropeptide by reversed-phase high-performance liquid chromatography on polystyrene-divinylbenzene", D. F. Elgar et al., Journal of Chromatography A 878 (2000) 183-196.

The protein sub-fractions eluted from the column may accurately be described by the composition of the buffer mixture or acetonitril content that effected their elution from the stationery phase. For example, soluble whey protein may be loaded onto a column filled with polystyrene-divinylbenzene beads (15 RPC TN 17-0727-02 from Amersham) a buffer A may be defined as 0.1 vol.-% trifluoroacetic acid (TFA) in water and a buffer B may be defined as 80 vol-% acetonitril and 0.85 vol.-% TFA (vol-%). Then, the mixing and transport of buffers A and B may be controlled by a specific system, for example a FPLC (Fast protein liquid chromatography) UNICORN station (Pharmacia /Amersham), and flown through the column.

The eluted protein sub-fraction may be defined by an elution range of mixing-ratios of the above mentioned buffers A and B. Using the specific buffer composition (because the elution order is pH dependent), the elution moment or interval of a protein sub-fraction may be described simply by the relative amount of acetonitrile present at the moment of elution of a protein fraction according to the invention.

If desirable, the sub-fractions thus obtained may be concentrated by techniques well known in the art, such as evaporation, ultrafiltration or dialysed to eliminate organic solvent before drying, for example by vacuum-, freeze-, spray-, fluidised bed-, oven-, or any other suitable drying process.

The sub-fractions listed in the examples in table 7 have been shown to be particularly effective in promoting COX II inhibition. According to an even more preferred embodiment the present invention relates to sub-fractions 1, 9, 10, and 14, as shown in table 5, which are highly effective.

Generally, milk of any mammalian origin (humans, cows, buffalos, sheep, goats, camels, horses, etc.) may be used for preparing the milk protein fractions or protein preparations according to the present invention.

Skimmed milk, acid whey and sweet whey may be prepared according to a process as described in the examples. The terms "soluble whey protein" or "soluble protein" as used in the context of the present invention means protein recovered in aqueous solution after an ultra-centrifugation (e.g. during 1 hr, at 100.000 g) or according to another process known to a skilled person. The terms "non-soluble protein" or "micellar casein" indicate the washed material recovered from the sediment after such an ultra centrifugation (e.g. according to the steps as lined out in example 1 or according to another process known to a skilled person).

Particularly, high cyclooxygenase-2 inhibiting activity are provided by sweet whey from human milk and by several fractions from cow milk, i.e. native, skimmed, sweet whey, soluble whey, sweet casein. For all three milk species investigated in the examples (human, bovine, buffalo), the highest COX-2 inhibition rates are obtained with sweet whey, which accordingly represents a preferred embodiment of the present invention.

Whey protein preparations provided good results, however were not as effective as several milk protein fractions. It may be thus assumed that in the milk protein fractions according to the present invention positive synergistic effects are provided enhancing the COX-2 inhibiting activity. If desired, the milk protein fractions and the whey protein preparations may also be combined.

Studies directed to the identification of the cyclooxygcnsc-2 inhibiting compound(s) present in the milk protein fractions according to the present invention showed that the compounds must be proteinaceous. Lactoferrin, a known compound has been shown not to have any cyclooxygense-2 inhibiting activity.

The bioavailability and the stability with respect to biodegradation of said one or more milk protein fractions and/or one or more milk protein preparations may be further increased by protecting one or more functional groups, such as e.g. —OH, —$NH_2$, —SH, —COOH, of compounds present in said one or more milk protein fractions and/or one or more milk protein preparations. Such protection may be performed e.g. by a reaction with one or more sugars or carbohydrates, such as e.g. lactose. For example, a heating of milk proteins in the presence of lactose yields lactosylated proteins. After protection, the compounds will provide an increased resistance against degradation, in particular a proteolytic degradation in the body which in turn generally results in an increased bioavailability. A derivatization may also be used to obtain a desired solubility and thereby a desired and controlled bioavailability.

According to another aspect, the present invention pertains to the use of one or more milk protein fractions and/or one or more milk protein preparations for the preparation of a nutritional or pharmaceutical composition for the treatment of COX-2 mediated diseases, by inhibiting the activity of cyclooxygenase-2.

The one or more milk protein fractions and/or one or more milk protein preparations providing COX-2 inhibiting activity may e.g. be administered in a oral, topical, parenteral, or rectal dosage form containing conventional non-toxic pharmaceutically acceptable carriers, excipients, adjuvants and vehicles. The term parenteral as used herein includes subcutaneous injections, intravenous, intramuscular, intrasternal injection or infusion techniques.

The nutritional or pharmaceutical composition according to the present invention may be used for treating or preventing cyclooxygenase-2 mediated diseases, such as cancer or pre-cancerous states, in particular of the colon, stomach, esophagus, liver, biliary stem, pancreas, head and neck, lung, breast, bladder, female genital organs' and skin and/or inflammatory diseases, such as arthritis, rheumatic fever, symptoms associated with influenza or other viral infections, dysmenorhea, headache, toothache, degenerative joint diseases, etc. and/or Alzheimer's disease.

Additionally, the nutritional or pharmaceutical composition according to the present invention may be applied as a co-treatment during a conventional cancer treatment and/or a treatment of a pre-cancerous state, a chemotherapy, a radiation therapy, a biotherapy and/or during the treatment of an inflammatory disease and/or during the treatment of Alzheimer's disease.

The one or more milk protein fractions and/or one or more milk protein preparations providing a cyclooxygenase-2 inhibiting activity may also be useful as a partial or complete substitute for conventional medicaments, such as e.g. NSAID'S. Thus, the invention comprises pharmaceutical compositions for treating cyclooxygenase-2 mediated diseases as defined above comprising a therapeutically effective amount of the said one or more milk protein fractions and/or one or more milk protein preparations and one or more therapeutically effective ingredients, such as a pain reliever; a potentiator; a H2-antagonist, a decongestant; an antitussive; a diuretic; a sedating or non-sedating antihistamine; an agent for treating or preventing cancer and/or precancerous states, etc.

The pharmaceutical compositions containing the active ingredient(s) may be in any form suitable for oral use, such as e.g. tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient(s) in admixture with non-toxic pharmaceutically acceptable excipients, such as inert diluents, granulating, disintegrating and lubricating agents, which are suitable for the manufacture of tablets. The tablets may be uncoated or they may be coated by known techniques to delay disintegration and absorption in the gastrointestinal tract and thereby provide a sustained action over a longer period.

Formulations for oral use may also be presented as hard gelatin capsules wherein the active ingredient is mixed with an inert solid diluent, or as soft gelatin capsules wherein the active ingredients is mixed with water or an oil medium.

Aqueous suspensions contain the active material in admixture with excipients suitable for the manufacture of aqueous suspensions, such as e.g. suspending agents, dispersing or wetting agents, preservatives, coloring agents, flavoring agents, and sweetening agents.

Dispersible powders and granules suitable for preparation of an aqueous suspension by the addition of water provide the active ingredient(s) in admixture with a dispersing or wetting agent, suspending agent and one or more preservatives. Additional excipients, for example sweetening, flavoring and coloring agents, may also be present.

The milk protein fractions and/or the milk protein preparations as illustrated above may be used in any nutritional, pharmaceutical or functional food composition, which compositions may comprise e.g. at least one component from the group consisting of water, proteins and/or peptides, fats and carbohydrates. Said composition may further comprise minerals and vitamins, e.g. in an amount of form 30% to 150% of the daily dosage according to U.S. RDA. In addition thereto, such compositions may comprise fiber material, flavoring agents, emulgators, radical scavengers, preservatives, acids, lipids, fruits and fruit juices, teas, etc.

In particular, the compositions according to the present invention may comprise e.g. a food composition selected from milk, yogurt, curd, cheese, fermented milks, milk based fermented products, ice-creams, cereal based products, milk based powders, infant formulae or pet food.

Formulations which may be expected to be highly accepted by the consumers are for example drinks, e.g. on basis of dairy products, conventional beverages, such as water, fruit juices or teas, comprising the milk protein fractions and/or preparations according to the present invention.

Additional examples for advantageous formulations are e.g. compositions in form of dessert preparations, gels or foams (such as e.g. "mousses" ("foams"), blancmanges, jellies, flans, preparations on yoghurt basis) or in form of snacks comprising a bakery product having a filling or center comprising the milk protein fractions and/or preparations according to the present invention. The milk protein fractions and/or preparations according to the present invention may also e.g. be applied in form of a top layer or coating on any conventional food product or be included as a filling material in any conventional food product.

According to another aspect, the present invention provides a process for increasing the cyclooxygenase-2 inhibiting activity of a product, said method comprising the step of increasing the amount of one or more milk protein fractions and/or one or more milk protein preparations providing a cyclooxygenase-2 inhibiting activity in said product.

The product wherein the cyclooxygenase-2 inhibiting activity is increased may be a e.g. a nutritional and/or a pharmaceutical and/or a functional food composition, in particular a dairy food product.

The present inventors also found processes for isolating milk protein fractions, which provide both good yields and essentially conserve the cyclooxygenase-2 inhibiting activity of the active components in said milk protein fractions.

The process for isolating sweet whey protein or acid whey protein providing a cyclooxygenase-2 inhibiting activity comprises the following steps: centrifuging milk at 13.600 g during 30 minutes for obtaining a cream layer and a layer of skimmed milk; separating said cream layer; isolating said skimmed milk; adding an aqueous solution of $CaCl_2$ in an amount to the skimmed milk such that a mixture having a concentration of 2 mmol/l $Ca^{2+}$ is obtained; heating said mixture to 35° C. and adding rennet having an activity of 50 mg active chymosine per liter (e.g. in an amount of 0.4 to 0.6, preferably 0.5 μl rennet per ml of skimmed milk) to said mixture or heating said mixture to 25° C. and acidifying said mixture to a pH of 4.6 with an aqueous solution of HCl (32%); centrifuging the mixture at 13 600 g during 30 minutes in order to obtain a phase separation; and isolating sweet whey protein or acid whey protein, respectively.

The process for isolating soluble whey protein providing a cyclooxygenase-2 inhibiting activity comprises the following steps: centrifuging milk at 13.600 g during 30 minutes for obtaining a cream layer and a layer of skimmed milk; separating said cream layer; isolating said skimmed milk; adding an aqueous solution of $CaCl_2$ in such an amount to the skimmed milk that a mixture having a concentration of 2 mmol/l $Ca^{2+}$ is obtained; centrifuging during 1 hour at 100.000 g for separating soluble whey protein phase from the non soluble micellar casein phase; and isolating soluble whey protein phase.

According to yet another aspect, the present invention pertains to a milk fraction providing a cyclooxygenase-2 inhibiting activity, said milk fraction being obtainable according to one of the processes as outlined above.

Due to their cyclooxygenase-2 inhibiting activity the milk protein fraction according to the present invention will provide alternatives to conventional NSAIDs, in particular in cases where such NSAIDs are contra-indicated, such as in cases of individuals suffering from ulcers, coagulation disorders, kidney diseases, etc. In addition, it may be expected that such a product will essentially be free of deleterious side effects and may therefore be consumed even over a long period of time. This will in particular be of high interest when a prevention of a cyclooxygenase-2 mediated disease is desired, e.g. in case of persons presumed to have an increased risk of developing cancer due to their genetic pre-disposition or due to an exposure to well known risk factors (high risk nutrition such as e.g. a typical "Western diet" high in fats and low in fibers, exposure to chemicals, etc.).

As milk products have been consumed since ages by mankind, it may be expected that a functional food or medicament according to the present invention will be highly accepted by the consumers.

The following examples illustrate the invention without limiting it to the specific embodiments mentioned.

EXAMPLES

All solvents were of analytical or HPLC grade and were purchased from Merck (Dietikon, Switzerland). Water was either purified in-house using a Millipore Milli-Q water purification system (Millipore, Volketswil, Switzerland) or was HPLC-grade (Merck, Darmstadt, Germany). $CaCl_2 \times 2\ H_2O$, HCl (32%), sodium hydroxide, perhydrol 30% $H_2O_2$ p. A. were all from Merck.

Rennet ("presure simple") was produced by TEXEL (38470 Vinay, France) and was obtained from Rhône Poulenc Rohrer (Cooperation Pharmaceutique Francaise, 77000 Melun, France; Batch No. 101089007) with an activity of 50 mg active chymosine per liter.

Example 1

Milk Sample Preparation

Standard steps for the preparation of milk fractions were performed as described in: C. Alais, *Science du Lait, Principe des Techniques Laitieres*. SEPAIC, Paris, 4$^{th}$ ed., 1984, p. 29-35 and 159-178, unless explicitly indicated otherwise.

The indicated laboratory-scale fractionation steps were developed starting from conventional, industrial milk processes. Surprisingly, the selectivity and separation efficacy could be significantly increased by performing the below indicated process steps, in particular by performing a centrifugation at high acceleration rates and specifically adapted washing steps.

1.1 Bovine Milk

Bovine milk was obtained from a local market ("Toni lait", Switzerland).

In a first step, cream was extracted from whole milk by means of a centrifugation having an acceleration rate up to 13 600 g using fixed angle rotor Sorval GS3 (9 000 rpm, during 30 minutes). Starting from 2.200 ml of whole milk, 90 g of cream were recovered in the top layer. After separation of the top layer, 2090 ml of skimmed milk were obtained.

The separation of sweet whey from casein is achieved by enzymatic treatment of skimmed milk inducing casein clotting. 520 µl of a 200 mM (200 mmol/l) aqueous solution of $CaCl_2$ were added to 520 ml of skimmed milk in order to reach a mixture having a final concentration of 2 mM (mmol/l) of $Ca^{2+}$. This skimmed milk mixture was heated at 35° C. and then 250 µl of rennet were immediately added under moderate magnetic stirring. After 1 min the blend was incubated during 50 min (minute(s)) at 35° C. in a water bath, poured in bottles for centrifugation and subsequently centrifuged during 30 minutes at 13.600 g (fixed angle rotor Sorval GS3; 9 000 rpm, 30 min) in order to separate sweet whey from the non-soluble rennet casein.

The 476 ml of supernatant (i.e. the "sweet whey") were fractionated in 10×1.3 ml aliquots (Eppendorf) and 40 ml plastic tubes, which were labelled (Sweet whey), frozen by immersion in liquid nitrogen and stocked in plastic bag at minus 20° C.

The rennet casein (45 g) was dispersed in 286 ml of an aqueous solution of 2 mM (mmol/l) $CaCl_2$, said $CaCl_2$-solution being supplemented with 0.9% by weight NaCl and then centrifuged; the supernatant (246 ml) was aliquoted into containers, which were labelled (Rennet casein wash) and frozen in liquid nitrogen.

The 31 g recovered, washed rennet casein were dispersed in an aqueous solution of 2 mM (mmol/l) $CaCl_2$, said $CaCl_2$-solution being supplemented with 0.9% by weight NaCl, such that a volume of 250 ml was obtained. The mixture was then aliquoted in containers, which were labeled (Rennet casein) and frozen.

The separation of acid whey from casein is obtained by chemical acidification of skimmed milk inducing casein clotting. 520 µl of an aqueous 200 mM (mmol/l) $CaCl_2$ solution were added to 520 ml of skimmed milk in order to reach a mixture having a final concentration of 2 mM (mmol/l) $Ca^{2+}$. This mixture was acidified at 25° C. by addition of an aqueous solution of HCl (32%) from pH 6.6 to pH 4.6 under moderate magnetic stirring. After 1 min of stirring, the blend was incubated during 60 min at 25° C., poured in bottles for centrifugation and subsequently centrifuged during 30 min at 13 600 g (fixed angle rotor Sorval GS3; 9 000 rpm, during 30 min) to separate acid whey from the non soluble acid casein.

The 503 ml of supernatant (i.e. the acid whey) were fractionated in 10×1.3 ml aliquots (Eppendorf) and 40 ml plastic tubes, which were labeled (Acid whey) and frozen by immersion in liquid nitrogen and stocked in plastic bag at −20° C.

The acid casein (41 g) was dispersed in 233 ml of an aqueous solution of 20 mM (mmol/l) sodium acetate having pH 4.6. The mixture thus obtained was centrifuged, and the supernatant (250 ml) was separated, and subsequently aliquoted into containers, which were labeled (Acid casein wash) and frozen in liquid nitrogen.

The 28.6 g recovered, washed acid casein were dispersed in water. The pH of this mixture was adjusted from 4.67 to 6.6 by an addition of NaOH. Subsequently, the volume was adjusted to 250 ml, and the so obtained mixture was aliquoted into containers, which were labeled (Acid casein) and frozen.

In order to separate soluble (whey) proteins and washed non-soluble proteins (micellar casein), the following steps were performed:

250 µL of an aqueous 200 mM (mmol/l) $CaCl_2$ solution were added to 250 ml of skimmed milk to obtain a mixture having a final concentration of 2 mM (mmol/l) of $Ca^{2+}$. This milk was ultra-centrifuged (6 tubes containing 42.1 g of skimmed milk in a fixed angle rotor 45 TI were centrifuged during 1 h in a Beckman L8-60M ultracentrifuge at a speed of 32 000 rpm corresponding to 100 000 g in the middle of the tube) in order to separate soluble whey protein from the non soluble micellar casein.

The 228 ml of supernatant (i.e. the soluble whey protein) were fractionated in 10×1.3 ml aliquots (Eppendorf) and 40 ml plastic tubes, which were labeled (Soluble whey protein) and frozen by immersion in liquid nitrogen and stocked in plastic bag at minus 20° C.

The micellar casein (24 g) was dispersed in 220 ml of an aqueous solution of 2 mM (mmol/l) $CaCl_2$, said $CaCl_2$-solution being supplemented with 0.9% by weight NaCl. The mixture was ultra-centrifuged (in a Beckman L8-60M ultracentrifuge during 1 hr at a speed of 32.000 rpm corresponding to 100.000 g in the middle of the tube. The supernatant (229 ml) was separated, and then aliquoted into containers, which were labeled (micellar casein wash) and frozen in liquid nitrogen.

The 22 g recovered, washed micellar casein were dispersed in an aqueous solution of 2 mM (mmol/l) $CaCl_2$, said $CaCl_2$-solution being supplemented with 0.9% by weight NaCl, so that a final volume of 250 ml was obtained. This mixture was aliquoted into containers, which were labeled (micellar casein) and frozen.

1.2. Human Breast Milk

Human breast milk was obtained from healthy mothers who agreed to donate breast-milk samples in quantities that did not jeopardize the nutritional supply of the baby (10-60 ml). Samples were obtained up to 70 days postpartum by breast pump expression or occasionally by manual expression and were processed within 2 hrs after collection. When not indicated explicitly otherwise, all procedure steps were performed as described in 1.1, above.

7.2 ml of an aqueous solution of 200 mM (mmol/l) $CaCl_2$ were added to 715 ml of whole milk in order to obtain a mixture of a final concentration of 2 mM (mmol/l) $Ca^{2+}$. After a centrifugation for cream separation (as described in 1.1., above), 26.6 g of cream were recovered as top layer and 713 g of skimmed milk were separated.

The separation sweet whey/casein is obtained by enzymatic treatment of skimmed milk inducing casein clotting. Skimmed milk (200 g) was heated at 35° C., and then 100 µl of rennet were immediately added under moderate magnetic stirring. After 1 min the blend was incubated during 50 min at 35° C. in a water bath, poured in bottles for centrifugation and subsequently centrifuged at 13.600 g during 30 min (as described in 1.1.) in order to separate sweet whey from the non-soluble rennet casein.

The 199 ml of supernatant (i.e. the sweet whey) were fractionated in 10×1.3 ml aliquots (Eppendorf) and 40 ml plastic tubes, which were labeled (Sweet whey) and frozen by immersion in liquid nitrogen and stocked in plastic bag at −20° C.

The rennet casein (2 g) was dispersed in 98 ml of an aqueous solution of 2 mM (mmol/l) $CaCl_2$, said $CaCl_2$-solution being supplemented with 0.9% by weight NaCl. The resulting mixture was centrifuged; the supernatant (99 ml) was separated and then aliquoted into containers, which were labeled (rennet casein wash) and frozen in liquid nitrogen.

The 1.15 g recovered rennet casein were dispersed in an aqueous solution of 2 mM (mmol/l) $CaCl_2$, said $CaCl_2$-solution being supplemented with 0.9% by weight volume NaCl, in order to obtain a volume of 100 ml. The resulting mixture was then aliquoted into containers, which were labeled (rennet casein) and frozen.

The separation of acid whey from casein is obtained by chemical acidification of skimmed milk inducing casein clotting. 200 ml of skimmed milk were acidified at 25° C. by addition of an aqueous solution of HCl (32%) from pH 6.6 to pH 4.6 under moderate magnetic stirring. After 1 min of stirring, the blend was incubated during 60 min at 25° C., poured in bottles for centrifugation and subsequently centrifuged at 13 600 g during 30 min (as described in Example 1.1) in order to separate acid whey from the non soluble acid casein.

The 195 ml of supernatant (i.e. acid whey) were fractionated in 10×1.3 ml aliquots (Eppendorf) and 40 ml plastic tubes, which were labeled (Acid whey) and frozen by immersion in liquid nitrogen and stocked in plastic bag at minus 20° C.

The acid casein (4.9 g) was dispersed in 95 ml of an aqueous solution of 20 mM (mmol/l) sodium acetate having pH 4.6, and the mixture was centrifuged. The supernatant (96 ml) was aliquoted into containers, which were labeled (Acid casein wash) and frozen in liquid nitrogen.

The 2.9 g recovered, washed acid casein were dispersed in 95 ml water. The pH of this mixture was adjusted to 6.2 by addition of NaOH. Subsequently, the volume was adjusted to 100 ml. The mixture was then aliquoted into containers, which were labeled (Acid casein) and frozen.

In order to separate soluble (whey) proteins and washed non-soluble proteins (micellar casein), the following steps were performed:

Skimmed milk was ultra-centrifuged as described under 1.1.

The 198 ml of supernatant were fractionated in 10×1.3 ml aliquots (Eppendorf) and 40 ml plastic tubes, which were labeled (Soluble whey protein) and frozen by immersion in liquid nitrogen and stocked in plastic bag at minus 20° C.

The micellar casein (0.5 g) was dispersed in 32 ml of an aqueous solution of 2 mM (mmol/l) $CaCl_2$, said $CaCl_2$-solution being supplemented with 0.9% by weight NaCl, and ultra-centrifuged (as described under Example 1.1). The so obtained supernatant (32.8 ml) was aliquoted into containers, which were labeled (micellar casein wash) and frozen in liquid nitrogen.

The 0.4 g recovered, washed micellar casein were dispersed in an aqueous solution of 2 mM (mmol/l) $CaCl_2$, said $CaCl_2$-solution being supplemented with 0.9% by weight NaCl, in order to obtain a volume of 33 ml. The resulting mixture was aliquoted into containers, which were labeled (micellar casein) and frozen.

1.3. Buffalo Milk

Pure fresh buffalo milk was obtained in the Lahore region of Pakistan and supplied refrigerated to a nearby laboratory where it was freeze-dried. Freezing temperature was about −20° C. to about −25° C. and the drying temperature was 40° C. The vacuum pressure was maintained below 2 Torr, with a final pressure of 0.2 Torr. The dried powder was sealed in aluminum-coated plastic bags, shipped and then stored at room temperature. When not indicated explicitly otherwise, all procedure steps were performed as described in Example 1.1.

The freeze-dried buffalo milk was reconstituted at 13% total solids (TS) by dissolving 70 g of the powder in 468 ml H20, and adding 5.4 ml of an 200 mM (200 mmol/l) aqueous solution of $CaCl_2$. 543 ml of reconstituted buffalo milk having a final concentration of 2 mM of $Ca^{2+}$ were obtained. After a centrifugation for cream separation as outlined under Example 1.1., 46 g of cream were recovered as a top layer and 485 ml of skimmed milk were separated.

The separation of sweet whey from casein was obtained by enzymatic treatment of skimmed milk inducing casein clotting. 145 ml of skimmed milk were heated at 35° C., then 73 µl of rennet were immediately added under moderate magnetic stirring. After 1 min the blend was incubated during 50 min at 35° C. in a water bath, poured in bottles for centrifugation and subsequently centrifuged during 30 min at 13 600 g (as described in Example 1.1) in order to separate sweet whey from the non-soluble rennet casein.

The 130 ml of supernatant (i.e. sweet whey) were fractionated in 10×1.3 ml aliquots (Eppendorf) and 40 ml plastic tubes, which were labeled (Sweet whey) and frozen by immersion in liquid nitrogen and stored in plastic bag at −20° C.

The rennet casein (14 g) was dispersed in 140 ml of an aqueous solution of 2 mM (mmol/1) $CaCl_2$, said $CaCl_2$-solution being supplemented with 0.9% by weight NaCl, and centrifuged (as outlined in Example 1.1). The so obtained supernatant (130 ml) was aliquoted into containers, which were labeled (rennet casein wash) and frozen in liquid nitrogen.

The 13 g recovered, washed rennet casein were dispersed in an aqueous solution of 2 mM (mmol/l) $CaCl_2$, said $CaCl_2$-solution being supplemented with 0.9% by weight NaCl, in order to obtain a volume of 145 ml. The resulting mixture was then aliquoted into containers, which were labeled (rennet casein) and frozen.

The separation acid whey/casein is obtained by chemical acidification of skimmed milk inducing casein clotting. 145 ml of skimmed milk were acidified at 25° C. by addition of 0.6 ml of an aqueous solution of HCl (32%) from pH 6.74 to pH 4.6 under moderate magnetic stirring. After 1 min of stirring, the blend was incubated during 60 min at 25° C., poured in bottles for centrifugation and subsequently centrifuged during 30 min at 13 600 (as described under Example 1.1) in order to separate acid whey from the non soluble acid casein.

The 129 ml of supernatant were fractionated in 10×1.3 ml aliquots (Eppendorf) and 40 ml plastic tubes, which were labeled (Acid whey) and frozen by immersion in liquid nitrogen and stocked in plastic bag at minus 20° C.

The acid casein (13 ) was dispersed in 130 ml of an aqueous solution of 20 mM (mmol/1) sodium acetate having pH 4.6, and the mixture was centrifuged (see Example 1.1). The supernatant (129 ml) was aliquoted into containers, which were labeled (Acid casein wash) and frozen in liquid nitrogen.

The 12 recovered, washed acid casein were dispersed in water and the pH was adjusted to 6.7 by addition of NaOH.

Subsequently, the volume was adjusted to 145 ml. The mixture was then aliquoted into containers, which were labeled (Acid casein) and frozen.

In order to separate soluble proteins and washed non-soluble proteins (micellar casein), the following steps were performed:

145 ml of skimmed buffalo milk were ultra-centrifuged (as described in Example 1.1) to separate whey from the non-soluble micellar casein. The 132 ml of supernatant were fractionated in 10×1.3 ml aliquots (Eppendorf) and 40 ml plastic tubes, which were labeled (Soluble whey protein) and frozen by immersion in liquid nitrogen and stocked in plastic bag at minus 20° C.

The gelatinous micellar casein (11.4 g) was dispersed in 133 ml of an aqueous solution of 2 mM (mmol/l) $CaCl_2$, said $CaCl_2$-solution being supplemented with 0.9% by weight NaCl. The mixture was ultra-centrifuged (see 1.1., above). The supernatant thus obtained (125 ml) was aliquoted into containers, which were labeled (micellar casein wash) and frozen in liquid nitrogen.

The 11 recovered, washed micellar casein were dispersed in an aqueous solution of 2 mM (mmol/l) $CaCl_2$, said $CaCl_2$-solution being supplemented with 0.9% by weight NaCl, in order to obtain a volume of 145 ml. The resulting mixture was then aliquoted into containers, which were labeled (micellar casein) and frozen.

Example 2

Sub-Fractionation of Soluble Whey Protein from Bovine Milk 15 ml of soluble whey protein obtained as described in example 1 were thawed for 20 min in a water-bath at 37° C., mixed by vortexing and centrifuged 1 min at 13.000 rpm in a 5415 Eppendorf centrifuge. After filtering on a 0.45 μm Millipore filter (306/GSWP04700.GS), 10 ml of this preparation was injected in a HR16×50 column filled with 100 ml Source 15 RPC TN 17-0727-02 (polystyrene-divinylbenzene), which was connected to a FPLC system controlled by a UNICORN station (Amersham Pharmacia Biotech).

The chromatographic conditions were:

A buffer: TFA 0.1% in water (2,000 ml of miliQ water filtered on a 0.45 μm Millipore system, plus 2 ml TFA (Sigma 91699, 100 ml));

B buffer: acetonitrile 80%, TFA 0.85% (400 ml of miliQ water filtered on a 0.45 μm Millipore system, plus 1.600 ml acetonitrile, degassed in an ultrasound bath during 15 minutes, and finally complemented with 1.7 ml TFA).

The column was equilibrated with 20% B buffer. Then, after one column volume (CV), sample was injected, B buffer increased to 75% in 15 CV and to 100% in 2.5 CV. At the end, gradient decreased to 20% B buffer in 0.4 CV. Flow rate was fixed at 3 ml/min.

96 fractions of 18 ml were collected in plastic tubes. The fractions were kept at −20° C. After HIC-HPLC analysis, the 96 collected tubes were pooled in 14 fractions by similitude of HPLC profile and concentrated by evaporation before lyophilisation for subsequent screening.

Table 1 shows 14 whey protein sub-fractions by a vol.-percentage range of buffer B, or a range in acetonitrile, within which sub-fractions are eluted.

TABLE 1

Sub-fractions of soluble whey protein defined by hydrophobic interaction chromatography

| % fraction | % B Buffer start | % B Buffer end | % acetonitrile start | % acetonitrile end |
|---|---|---|---|---|
| 1 | 20 | 26 | 16 | 20.8 |
| 2 | 26 | 35 | 20.8 | 28 |
| 3 | 35 | 43 | 28 | 34.4 |
| 4 | 43 | 44.5 | 34.4 | 35.6 |
| 5 | 44.5 | 47 | 35.6 | 37.6 |
| 6 | 47 | 48.5 | 37.6 | 38.8 |
| 7 | 48.5 | 50 | 38.8 | 40 |
| 8 | 50 | 51.5 | 40 | 41.2 |
| 9 | 51.5 | 52.5 | 41.2 | 42 |
| 10 | 52.5 | 54 | 42 | 43.2 |
| 11 | 54 | 58 | 43.2 | 46.4 |
| 12 | 58 | 60 | 46.4 | 48 |
| 13 | 60 | 70 | 48 | 56 |
| 14 | 70 | 100 | 56 | 80 |

Buffer A: Water TFA 0.1% Buffer B: Acetonitrile/Water/TFA (80%/19.15%/0.85%; v/v)
Column: Source 15 RPC Amersham (matrix: Polystyrene/divinyl benzene), column volume (CV = 100 ml)
Gradient: starting from 20% B Buffer, sample was injected after 1 column volume (CV), then gradient increased up to 75% B in 15 CV then 2 CV to reach 100% B Buffer

Example 3

COX-2 Screening 2.1 Material and Method

HUV-EC-C cells (a permanent endothelial cell line derived from the vein of a normal human umbilical cord; ATCC CRL1730; M. Miralpeix, M. Camacho et al., Brit. J. Pharmacol. 121 (1997), 171-180), were seeded onto 96-well plates (RPMI 1640+10% FCS) and treated with 100 nM (nmol/l) phorbol 12-myristate 13-acetate for 6 h at 37° C. to induce COX-2 isoenzyme. 50 μM (μmol/l) arachidonic acid were then added and the cells were incubated in the presence of test compounds or mixtures for 30 min at 37° C. Prostaglandine-E2 production was measured by radioimmuno assay (RIA) and the radioactivity determined with a scintillation counter (Topcount, Packard) using a liquid scintillation cocktail (Packard).

The results obtained are expressed as a percent of control values and as a percent inhibition of control values obtained in the presence of the test compounds. The control values correspond to the COX-2 activity of HUV-EC-C cells after stimulation with Phorbol Myristate Acetate (PMA) during 6 hours at 37° C. (can be done also with Tumor Necrosis Factor type alpha: TNFα) in absence of test compound.

The concentration causing a half-maximal inhibition of control values (IC50 value) and Hill coefficients (nH) were determined for the reference compounds (cycloheximide) by nonlinear regression analysis of their inhibition curves. These parameters were obtained by Hill equation curve fitting. The IC50 values obtained for the reference compounds were within accepted limits of historic averages obtained ±0.5 log units.

All COX-2 screening experiments were conducted once. In the following, inhibition values below 10% were not considered and have been indicated as "0".

2.2. COX-2 Screening of Human Milk Fraction

Skimmed human milk shows a significant COX-2 inhibition (25%; Table 2). When casein is removed by acidification or rennet (yielding acid whey and sweet whey, respectively), values of 51% and 58% COX-2 inhibition were achieved.

Thus, removing casein greatly improves COX-2 inhibition. In addition, the caseins alone (acid, sweet, micellar) do not show any inhibitory effect on COX-2.

Soluble whey from human milk performed just like the starting product (i.e., skimmed human milk).

TABLE 2

Results from COX-2 screening with human milk fractions.

| Skimmed Human Milk | Code | TS (mg/ml) | dilution for 50 µg/ml | estimated protein (mg/ml) | COX-2 inhibition in (%) |
|---|---|---|---|---|---|
| skimmed human Milk | H2 | 100 | 5.00E−04 | 10 | 25 |
| Acid whey human milk | H3 | 80 | 6.25E−04 | 6 | 51 |
| sweet whey HM | H4 | 80 | 6.25E−04 | 6 | 58 |
| soluble whey HM | H5 | 80 | 6.25E−04 | 6 | 26 |
| Acid casein HM | H6 | 10 | 5.00E−03 | 10 | 0 |
| sweet casein HM | H7 | 10 | 5.00E−03 | 10 | 0 |
| micellar casein HM | H8 | 5 | 1.00E−02 | 5 | 0 |

TS, total solids

2.3 COX-2 Screening of Buffalo Milk

Skimmed buffalo milk shows a medium inhibitory effect (36%; Table 3). In contrast to human milk, the acid removal of caseins leads to a loss of two thirds of its activity (down to 12%), probably due to an acid-induced loss of activity after acidification. If the pH is kept constant (i.e. in case of rennet treatment and ultra-centrifugation), activity increases to 44% in both cases.

As with human milk, micellar buffalo milk caseins did not show any activity. Acid and sweet caseins were not tested due to their lack of solubility.

TABLE 3

Results from COX-2 screening with buffalo milk.

| Buffalo Milk (BM) | Code | TS (mg/ml) | dilution for 50 µg/ml | Estimated protein (mg/ml) in sample | COX-2 inhibition (%) |
|---|---|---|---|---|---|
| skimmed buffalo milk (BM) | B2 | 100 | 5.00E−04 | 30 | 36 |
| acid whey BM | B3 | 70 | 7.14E−04 | 6 | 12 |
| sweet whey BM | B4 | 70 | 7.14E−04 | 6 | 44 |
| soluble whey BM | B5 | 70 | 7.14E−04 | 6 | 44 |
| acid casein BM | not soluble | | | | |
| sweet casein BM | not soluble | | | | |
| micellar casein BM | B8 | 25 | 2.00E−03 | 25 | 0 |

TS, total solids

2.4 COX-2 Screening of Cow Milk

The high activities of raw and skimmed cow's milk (52-53%; Table 4) demonstrate that the elimination of cream does not have any effect on COX-2 inhibition. Activity remains constant in soluble whey (53%), decreases slightly in acid whey (45%) and increases in sweet whey (68%). Without wishing to be bound to any theory, the decrease of the activity in acid whey may, as in buffalo milk, be related to the influence of the acid, whereas the increase of activity upon rennet treatment could be explained by the theory that the casein destabilisation releases some "latent" bioactivity, like it is sometimes described during "fractionation failing", leading to a yield higher than 100%.

TABLE 4

Results from COX-2 screening with bovine milk.

| Cow's milk (CM) | Code | TS (mg/ml) | dilution for 50 µg/ml | Protein (mg/ml) estimated in sample | COX-2 inhibition (%) |
|---|---|---|---|---|---|
| cow's milk CM | C1 | 100 | 5.00E−04 | 31 | 53 |
| skimmed CM | C2 | 100 | 5.00E−04 | 35 | 52 |
| acid whey CM | C3 | 70 | 7.14E−04 | 6 | 45 |
| sweet whey CM | C4 | 70 | 7.14E−04 | 6 | 68 |
| soluble whey CM | C5 | 70 | 7.14E−04 | 6 | 53 |
| acid casein CM | C6 | 50 | 1.00E−03 | 50 | 42 |
| sweet casein CM | C7 | 50 | 1.00E−03 | 50 | 65 |
| micellar casein CM | C8 | 25 | 2.00E−03 | 25 | 0 |

TS, total solids 2.5 COX-2 Screening of Whey Protein Preparations

Two commercially available whey protein preparations were also subjected to a COX-2 screening:

Lacprodan 80 (MD Foods Ingredients, Viby, Denmark) which contains high amounts of lactosyl β-lactoglobulin forms;

WPI 95, a native whey protein isolate which is virtually depleted in lactosyl β-lactoglobulin (verified by mass spectrometry). WPI is available from: Davisco Foods International. Inc. 620 North Main, Le Sueur, Minn. 56058 USA; BIPRO batch JE 251-0-420.

TABLE 5

Results from COX-2 screening with whey protein preparations.

| Whey protein preparation | Code | TS (mg/ml) | dilution for 50 μg/ml | protein (mg/ml) estimated in sample | COX-2 inhibition (%) |
|---|---|---|---|---|---|
| Lacprodan 80 | LN | 100 | 5.00E−04 | 80 | 23 |
| native whey | NW | 100 | 5.00E−04 | 95 | 33 |
| WPI 95 | | | | | |
| Cysteine | CY | 10 | 5.00E−03 | 10 | 0 |
| whey tryptic hydrolysate DM 10 | DH | 100 | 5.00E−04 | 80 | 0 |

TS, total solids

As may be derived from Table 4, also these compounds show a considerable COX-2 inhibition activity of 23% and 33%, respectively. In contrast thereto, a proteolysis by trypsin destroys the COX-2 inhibition activity of whey protein. Also, the natural "antioxidant amino acid" cysteine has no effect on COX-2 inhibition.

2.5. COX-2 Screening of Oxidized Bovine Milk

Samples of fresh bovine milk (50 ml) have been supplemented with perhydrol (30% $H_2O_2$) in order to obtain a final concentration of 0.1 MM, 1 mM, 10 mM, 100 mM (mmol/l) of $H_2O_2$ in the resulting mixture. All samples were incubated for 4 h at 30° C.

TABLE 6

Results from COX-2 screening with oxidized bovine milk.

| Protein Oxidation | Code | TS (mg/ml) | dilution for 50 μg/ml | protein (mg/ml) estimated in sample | COX-2 inhibition (%) |
|---|---|---|---|---|---|
| fresh bovine milk | | L1 | 100 | 5.00E−04 | 3.1 | 41 |
| fresh bovine milk $H_2O_2$ | 0.1 | L2 | 100 | 5.00E−04 | 3.1 | 41 |
| fresh bovine milk $H_2O_2$ | 1 | L3 | 100 | 5.00E−04 | 3.1 | 35 |
| fresh bovine milk $H_2O_2$ | 10 | L4 | 100 | 5.00E−04 | 3.1 | 27 |
| fresh bovine milk $H_2O_2$ mM | 100 | L5 | 100 | 5.00E−04 | 3.1 | 0 |

TS, total solids

Untreated bovine milk and milk treated with 0.1 mM $H_2O_2$ show the same "medium" effect on COX-2 inhibition (41%). At 1 mM $H_2O_2$, inhibition decreases slightly (to 35%), further increase to 10 mM reduces COX-2 inhibition to 27%, and at 100 mM $H_2O_2$—which is, however, far from physiologic conditions—no more inhibiting activity is observed at all.

The results indicate that the active, i.e. COX-2 suppressing component in bovine milk resists $H_2O_2$ at the level of 0.1-10 mM. The decrease of inhibitory effect correspond to the increase of protein oxidation, which indicates that the COX-2 inhibiting activity is protein based and strongly related to the native status of the protein.

2.6. COX-2 Screening of Sub-Fractions of Soluble Whey Proteins

The results of COX-2 inhibition by the soluble whey protein subfractions is indicated in table 7. Positive values indicate a better performance as compared to the control.

TABLE 7

Results of COX II inhibition

| HIC fraction | % inhibition of control values |
|---|---|
| 1 | 21 |
| 2 | −3 |
| 3 | −7 |
| 4 | 7 |
| 5 | −17 |
| 6 | −21 |
| 7 | −55 |
| 8 | 10 |
| 9 | 36 |
| 10 | 41 |
| 11 | 12 |
| 12 | 12 |
| 13 | 10 |
| 14 | 52 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A composition for treating cyclooxygenase-2 mediated diseases, the composition comprising a therapeutically effective amount of a sweet casein fraction of bovine milk that exhibits a cyclooxygenase-2 inhibiting activity, and wherein the composition further comprises a food material selected from the group consisting of milk, yogurt, curd, cheese, fermented milks, a milk based fermented product, an ice-cream, a cereal based product, a milk based product, infant formula, pet food and combinations thereof.

2. The composition according to claim 1, wherein the bioavailability and/or biodegradation stability of the sweet casein fraction of bovine milk is increased by protecting one or more functional groups in one or more components contained therein.

3. The composition according to claim 1 having a form selected from the group consisting of oral, topical, parenteral, rectal dosage form, and combinations thereof.

4. A method for preparing a food composition for treating cyclooxygenase-2 mediated diseases, the method comprising adding to food composition a therapeutically effective amount of a sweet casein fraction of bovine milk that exhibits a cyclooxygenase-2 inhibiting activity.

5. The method according to claim 4, wherein the cyclooxygenase-2 mediated diseases are selected from the group consisting of cancer pre-cancerous states, and inflammatory diseases, and symptoms associated with influenza or other viral infections, dysmenorrhoea, headache, toothache, degenerative joint diseases, Alzheimer's disease, and combinations thereof.

6. The method according to claim 4, wherein the composition provides a co-treatment during a treatment selected from the group consisting of cancer treatment, a treatment of a pre-cancerous state, a pain treatment, a treatment of an inflammatory disease, treatment of Alzheimer's disease, and combinations thereof.

7. The method according to claim 4, wherein the food composition is selected from the group consisting of milk, yogurt, curd, cheese, a milk based fermented product, an ice-cream, a cereal based product, a milk based powder, infant formula, pet food and combinations thereof.

8. The method of claim 6, wherein the co-treatment is selected from the group consisting of chemotherapy, radiation therapy, biotherapy, and combinations thereof.

9. The composition according to claim 1, wherein said therapeutically effective amount of the sweet casein fraction of bovine milk is between about 0.1 mg and 1 g per day per kilogram of body weight of an individual having a cyclooxygenase-2 mediated disease.

10. The method according to claim 4, wherein said therapeutically effective amount of the sweet casein fraction of bovine milk that is added to the composition is between about 0.1 mg and 1 g per day per kilogram of body weight of an individual having a cyclooxygenase-2 mediated disease.

* * * * *